(12) United States Patent
Chen (10) Patent No.: US 11,200,982 B2
(45) Date of Patent: Dec. 14, 2021

(54) METHOD FOR ANALYSING MEDICAL TREATMENT DATA BASED ON DEEP LEARNING AND INTELLIGENCE ANALYSER THEREOF

(71) Applicant: Infervision Medical Technology Co., Ltd., Beijing (CN)

(72) Inventor: Kuan Chen, Beijing (CN)

(73) Assignee: Infervision Medical Technology Co., Ltd., Beijing (CN)

( * ) Notice: Subject to any disclaimer, the term of this patent is extended or adjusted under 35 U.S.C. 154(b) by 673 days.

(21) Appl. No.: 15/579,212

(22) PCT Filed: May 31, 2016

(86) PCT No.: PCT/CN2016/084000
§ 371 (c)(1),
(2) Date: Dec. 3, 2017

(87) PCT Pub. No.: WO2016/192612
PCT Pub. Date: Dec. 8, 2016

(65) Prior Publication Data
US 2018/0137941 A1    May 17, 2018

(30) Foreign Application Priority Data

Jun. 2, 2015    (CN) .......................... 201510294286.3

(51) Int. Cl.
*G16H 50/20*      (2018.01)
*G16H 50/50*      (2018.01)
(Continued)

(52) U.S. Cl.
CPC .............. *G16H 50/20* (2018.01); *G06N 3/04* (2013.01); *G06N 3/08* (2013.01); *G06N 3/088* (2013.01);
(Continued)

(58) Field of Classification Search
None
See application file for complete search history.

(56) References Cited

U.S. PATENT DOCUMENTS

| 5,687,716 A | * | 11/1997 | Kaufmann | ............. | G06F 19/00 600/300 |
| 2005/0049497 A1 | * | 3/2005 | Krishnan | ............... | G16H 50/20 600/437 |

(Continued)

FOREIGN PATENT DOCUMENTS

| CN | 1194045 A | 9/1998 |
| CN | 1943508 A | 4/2007 |

(Continued)

OTHER PUBLICATIONS

Stiensaltz, David, Locally Contractive Iterated Function System, 1999, The Annals of Probablity, vol. 27, No. 4, pp. 1952-1979 (Year: 1999).*

(Continued)

*Primary Examiner* — Devin C Hein
(74) *Attorney, Agent, or Firm* — Westbridge IP LLC (57) ABSTRACT

A method for analysing medical treatment data based on deep learning via an intelligent analyser thereof, effectively alleviates work stress for doctors in a hospital or medical researchers and performs scientific analysis on a large amount of medical treatment data or medical data and obtain an analysis result matched therewith. The core content of the method is the establishment of a model in a computer using a deep convolution neuron algorithm in deep learning. The model assists the doctors to make correct judgments and effective decisions for the large amount of medical treatment data using mass medical treatment data selection and optimization model parameters by "training" the model to automatically learn a pathology analysis process of the (Continued)

doctors or the medical researchers and then helping them in processing the large amount of medical treatment data or medical data.

14 Claims, 4 Drawing Sheets

(51) Int. Cl.
  *G06N 3/04* (2006.01)
  *G06N 3/08* (2006.01)
  *G16H 30/40* (2018.01)
  *G16Z 99/00* (2019.01)

(52) U.S. Cl.
  CPC ............ *G16H 50/50* (2018.01); *G16Z 99/00* (2019.02); *G16H 30/40* (2018.01)

(56) References Cited

U.S. PATENT DOCUMENTS

| | | | |
|---|---|---|---|
| 2015/0112182 A1 | 4/2015 | Sharma et al. | |
| 2016/0073969 A1* | 3/2016 | Ithapu | A61B 6/5247 382/128 |
| 2016/0106321 A1* | 4/2016 | Sharma | A61B 6/5217 600/407 |
| 2016/0314580 A1* | 10/2016 | Lloyd | G06T 7/0012 |
| 2017/0124269 A1* | 5/2017 | McNair | G16H 10/60 |

FOREIGN PATENT DOCUMENTS

| | | |
|---|---|---|
| CN | 102542562 A | 7/2012 |
| CN | 203122364 U | 8/2013 |
| CN | 103544392 A | 1/2014 |
| CN | 103914841 A | 7/2014 |
| CN | 104298651 A | 1/2015 |
| CN | 104523266 A | 4/2015 |
| CN | 104866727 A | 8/2015 |
| JP | 2009210465 A | 9/2009 |
| WO | 2014152395 A1 | 9/2014 |

OTHER PUBLICATIONS

Bengio, Learning Deep Architectures for AI, Foundations and Trends in Machine Learning, Jan. 1, 2009.
Examination Report in counterpart European Patent Application No. 16802535.1, dated Nov. 2, 2020.
Fifth Office Action in counterpart Chinese Patent Application No. 201510294286.3, dated Sep. 21, 2018.
First Office Action in counterpart Chinese Patent Application No. 201510294286.3, dated Apr. 12, 2017.
Fourth Office Action in counterpart Chinese Patent Application No. 201510294286.3, dated May 29, 2018.
International Search Report in corresponding PCT Application No. PCT/CN2016/084000, dated Jun. 30, 2016.
Krizhevsky et al., ImageNet Classification with Deep Convolutional Neural Networks, Communications of the ACM, vol. 60, No. 6, May 24, 2017.
Lecun et al., Deep Learning, Nature, May 28, 2015, pp. 436-444, vol. 521, Issue 7553.
Moneta et al., Automated diagnosis and disease characterization using neural network analysis, Proceedings of the International Conference on Systems, Man, and Cybernetics, New York, IEEE, US, 1992, pp. 123-128.
Office Action in counterpart Japanese Patent Application No. 2017-559611, dated Jan. 28, 2019.
Second Office Action in counterpart Chinese Patent Application No. 201510294286.3, dated Sep. 12, 2017.
Third Office Action in counterpart Chinese Patent Application No. 201510294286.3, dated Jan. 15, 2018.
Written Opinion in corresponding PCT Application No. PCT/CN2016/084000, dated Jun. 30, 2016.

* cited by examiner

METHOD FOR ANALYSING MEDICAL TREATMENT DATA BASED ON DEEP LEARNING AND INTELLIGENCE ANALYSER THEREOF

CROSS REFERENCE OF RELATED APPLICATION

This is a U.S. National Stage under 35 U.S.C. 371 of the International Application Number PCT/CN2016/08400, filed May 31, 2016, which claims priority under 35 U.S.C. 119(a-d) to Chinese application number 201510294286.3, filed Jun. 2, 2015.

NOTICE OF COPYRIGHT

A portion of the disclosure of this patent document contains material which is subject to copyright protection. The copyright owner has no objection to any reproduction by anyone of the patent disclosure, as it appears in the United States Patent and Trademark Office patent files or records, but otherwise reserves all copyright rights whatsoever.

BACKGROUND OF THE PRESENT INVENTION

Field of Invention

The present invention relates to an intelligent device for analysing medical treatment data or medical data, more particularly to an intelligent analyser adapted for automatically summarizing a large amount of medical treatment data or medical data from hospital or medical research institution and generating an analysis result matched therewith.

Description of Related Arts

Generally, doctors or researchers at hospitals or medical research institutions need to complete a great deal of work every day. For instance, a doctor in a clinical department of a hospital needs to conduct research, analysis and decision-making on collected medical treatment data every day.

The following is a presentation of medical treatment data sampled on a random day from a tertiary hospital in Beijing, including 1162 cases of CT (Computer Tomography), 1461 cases of X-ray and 325 cases of NMR (Nuclear Magnetic Resonance), wherein each CT case includes 2 two-dimensional pictures averagely, each CT case includes 50 two-dimensional pictures averagely, and each NMR case includes 100 two-dimensional pictures in average.

All these detection data should be drafted into reports by radiologists, while there are merely about twenty radiologists in this tertiary hospital including typing-slowly older ones and inexperienced young ones. Consequently, the related doctors or researchers are under great work pressure with such large amount of continuous daily work, causing rapid energy-declining, low work efficiency and even high rate of error analysing conclusion.

SUMMARY OF THE PRESENT INVENTION

The technique problem solved in the present invention is to provide a method for analysing medical treatment data based on deep learning, and an intelligent analyser thereof, which can effectively alleviate work stress for doctors in a hospital or medical researchers and can perform scientific analysis on a large amount of medical treatment data or medical data and obtain an analysis result matched therewith.

In order to solve the above technique problem, the present invention provides a method for analysing medical treatment data based on deep learning, which comprises the following steps:

1) collecting and storing a large amount of registered medical treatment raw data and medical diagnosis raw data which is matched and of the same type with the medical treatment raw data as medical treatment training data at a computer device via an input device;

2) linking the variation value of the textual data and image data which is not less than two-dimension in the medical treatment training data with time and space with the corresponding data;

3) unifying the medical treatment training data and the variation value of each subject into one unit data in the step of collecting the large amount of medical training data;

4) transforming or formatting the medical treatment training data into computer-understandable structured data matrix by segmentation, correlation or text data mining methods, and extracting features from each unit data;

5) inputting the medical treatment data formed as structured data matrix into a corresponding deep learning model of the computer device at an storage module thereof;

6) optimizing the deep learning model via the computer device, wherein the optimization method comprises the following steps:

a. constructing a primary deep learning frame to establish a data model comprising an input layer, at least a hidden layer and an output layer, according to the features of the medical treatment training data, wherein the input layer comprises a plurality of nodes having a plurality of features of the medical treatment raw data, the output layer comprises a plurality of nodes with a plurality of features of the medical diagnosis data, and each hidden layer comprises a plurality of nodes mapping with an output from an previous layer thereof;

b. Constructing a data model for each node with a mathematical formula, wherein the related parameters for the formula are preset manually or at random automatically, the inputs to the nodes of the input layer are the features of the medical treatment training data, and the inputs to respective hidden layer and the output layer are the outputs generated at a previous layer thereof respectively, wherein the outputs at each node of each layer is obtained according to the mathematical formula thereof; and c. initializing the parameter Ai and comparing the output generated at each node of the output layer with the medical treatment diagnosis data stored at the respective node to modify the parameter Ai at the note thereby in a orderly-cycling manner to ultimately obtain a parameter Ai at the respective note which enables the output generated at the respective note of the output layer partial-maximally similar to the features of the medical treatment diagnosis data at corresponding node, 7) inputting the obtained to-be-analyzed medical data formed as structured matrix data, into the deep learning model to conduct a medical pathological analysis matched therewith; and 8) outputting a medical pathological analysis result matched with the to-be-analyzed medical data by the deep learning model through an output device.

The method to optimize the parameter Ai is unsupervised learning method. The unsupervised learning method uses a Denoising Autoencoder or Restricted Boltzmann Machine to self-learn.

The method to optimize the parameter Ai is supervised learning method. The mathematical formula can be a parametric mathematic formula or a non-parametric one, wherein the parametric formula can be linear model formula, neuron model formula or convolution operation, and the non-parametric one can be extreme formula. The mathematic model is constructed as follows:

$y=g(X)=fn\bigcirc fn-1\bigcirc fn-2\bigcirc \ldots \bigcirc f1(X)$, wherein the y is the features of the medical treatment diagnosis data at the output layer and the dimension thereof is $M_n$, the X is the training raw data and the dimension thereof is $M_0$, and the f1 to fn are the formulas for each layer, and the dimension for fi at the respective layer is Mi–1 to Mi, i.e., the f1 is arranged to transform the X in M0-dimensioned into the M1-dimensioned output Z1, wherein the Z1 is the input of the formula at f2 and as such in a forward-propagation manner. The model fi at each layer has a parameter Ai array matched therewith.

The medical raw data comprise the related records on patient diagnosis, detection and treatment by clinical doctors and medical technicians.

The medical treatment diagnosis data comprise the related records on initial diagnosis, discharge result and disease treatment effect by clinical doctors and medical technicians, and the textual visiting records and the follow-up data by the doctors.

The data features comprise the variation value of the medical treatment training data with time and space, and the varying mathematical statistics values of the data themselves, i.e., the decreasing or increasing trend of the data with respective to the time.

The structured data of the to-be-analyzed medical data and the medical analysis data matched therewith are fed back to deep learning model as new training data.

The present invention provides an intelligent analyzer for analyzing medical treatment data based on deep learning, comprising:

an inputting means for inputting the medical treatment training data and the to-be-analyzed medical data into a computer device;

an storage module for storing the medical treatment training data and the to-be-analyzed data separately or collectively;

a deep learning model module for calling the medical treatment training data stored at storage model for self-learning;

an outputting means for outputting the medical pathological analysis result matched with the to-be-analyzed medical data; and a CPU and/or GPU processor, wherein the medical treatment training data comprise a medical raw data and a medical treatment diagnosis data matched therewith and the medical treatment training data and the to-be-analyzed medical data are computer-understandable structured data matrix, wherein the self-learning of deep learning model module uses the parametrical mathematical formulas including linear model equation, neuron model equation, convolution equation, and/or extreme formulas, wherein the inputting means comprises computer devices provided at hospitals or medical research institutions, and stationary computing output terminals and portable intelligent terminals networked with the computer devices, wherein the output means comprises stationary computing output terminals and portable intelligent terminals provided at hospitals and medical research institutions and networked with the inputting means.

The intelligent analyzer further comprises a network linking module for linking to the internet or Ethernet by means of wire, WIFI model or GPRS module.

The core content of the method and the intelligent analyzer thereof is the establishment of a model in a computer using a deep convolution neuron algorithm in deep learning. The model assists the doctors to make correct judgments and effective decisions for the large amount of medical treatment data using mass medical treatment data selection and optimization model parameters by "training" the model to automatically learn a pathology analysis process of the doctors or the medical researchers and then helping them in processing the large amount of medical treatment data or medical data. The present invention can greatly reduce the work stress for the doctors or the medical researchers and improve the work efficiency thereof. The present invention can free the doctors or the medical researchers from heavy analysis work on the medical treatment data or medical data, so that they can put more effort into other more important work.

Still further objects and advantages will become apparent from a consideration of the ensuing description and drawings.

These and other objectives, features, and advantages of the present invention will become apparent from the following detailed description, the accompanying drawings, and the appended claims.

DETAILED DESCRIPTION OF THE PREFERRED EMBODIMENT

The following description is disclosed to enable any person skilled in the art to make and use the present invention. Preferred embodiments are provided in the following description only as examples and modifications will be apparent to those skilled in the art. The general principles defined in the following description would be applied to other embodiments, alternatives, modifications, equivalents, and applications without departing from the spirit and scope of the present invention.

Figure 1:
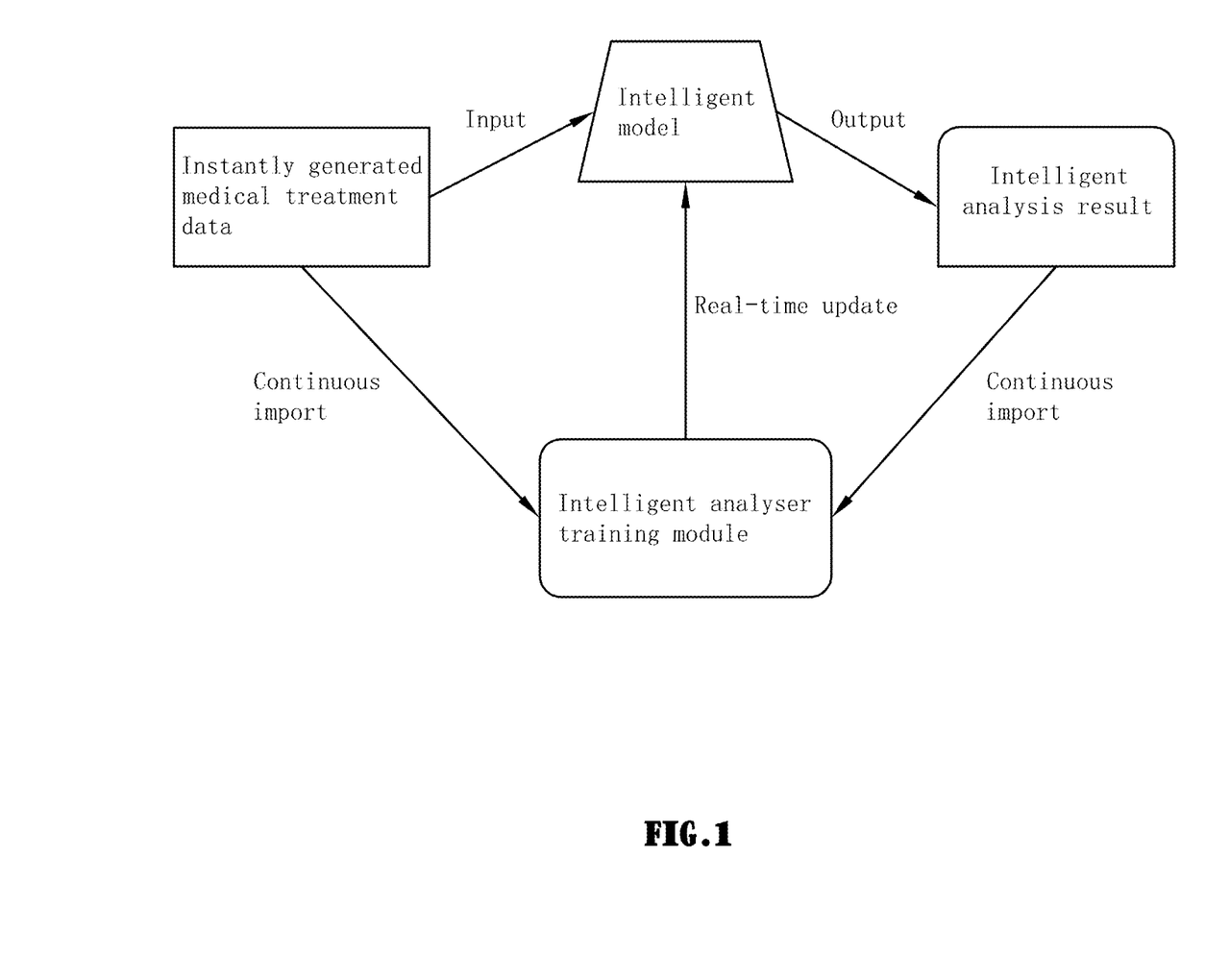
FIG. 1 is a block diagram of the operation of the intelligence analyser in the present invention.

Referring to FIG. 1 of the drawings, the present invention provides a method for analysing medical treatment data based on deep learning, which assists the doctors to made correct judgments and effective decisions for a large amount of medical treatment data using mass medical treatment data selection and model parameters optimization by "training" the model to automatically learn a pathology analysis process of the doctors or the medical researchers and then helping them in processing the large amount of medical treatment data or medical data.

Generally, medical treatment data intelligence analysis system is one of the most important areas in medical technology, i.e. the analysing system of medical treatment image data, where a large proportion of efforts are centralized at the pulmonary CT nodule analysis mainly comprising two technique modules, the image segmentation and intelligence detection. The main purpose of image segmentation is to assist clinical doctors and imaging physicians to better analyze the lung structure and prepared for the surgeon by segmenting key parts of the lung, such as trachea, lung lobes, blood vessels and then representing them in a 3D image model. Although, there are very mature technologies and algorithms in image segmentation, most of which are conventional model algorithms, such as cascade model, which is unable to make best of the intelligent analyser. Further, the analysis system for the image segmentation merely accounts for a minimal proportion of medical treatment data processing, and the significance thereof to the doctors is limited as well.

Deep learning technology regarding as a revolutionary technology in the field of artificial intelligence has subverted the conventional application methods in image recognition and speech recognition, and brought many breakthrough applications such as Google image content analysis, Google Driverless Car, Google book, and Google Brain, successfully.

However, the most common methods utilized in the medical treatment data analysis field are conventional classification method such as Support Vector Machine, instead of the most advanced technology in artificial intelligence field up to now. For example, the method adopted in a patent No. CN201110376737 X is Gradient Boosting method which is the most widely-used method in the machine learning method from 1995 to 2005 but is unable to present the most advanced technology in artificial intelligence field any more.

Recent, it is recognized that the most advanced algorithm in 2-D and 3-D image recognition is the Deep Neural Network ((see Bengio-2009, cited by Yoshua Bengio, "Learning Deep Architectures for AI", Foundations and in Machine Learning 2 (1), 1-127).). In some applications with massive training data, such as hand-writing number recognition and traffic light recognition, the machine may outperform than human-identification with a higher correct rate.

The invention applies the most advanced deep learning algorithms into medical treatment data analysis to construct a medical treatment data analysis system by using a large amount of data to establish models, which is able to substantially relief the work pressure for the doctors and improve their work efficiency.

The medical treatment data analysis system mainly comprises a model per-training module and a module fine-tuning module, wherein the model pre-training module is aimed to figure out a mathematical representation which best represents the medical treatment analysis process features using the medical treatment training data. The main application module in the intelligence analyser system is an application module, which is arranged to be inputted the to-be-analyzed medical treatment data into the pre-training module and generates a medical pathological analysis result matched with the to-be-analyzed medical treatment data automatically.

The following is the detailed descriptions of the present invention.

The method of the present invention comprises the following steps.

The first step is to collect and store massive registered medical treatment raw data and medical treatment diagnosis data which is matched and of the same type with the medical treatment raw data as medical treatment training data at a computer device via an input device. The purpose of medical treatment pre-training is to enable the computer device to figure out a corresponding medical treatment diagnosis analysis data automatically in responsive to the medical treatment raw data.

The medical treatment raw data comprises the related records on the patient diagnosis, detection and treatment by clinical doctors and medical technicians. The medical treatment diagnosis data comprise the related records on initial diagnosis, discharge result and disease treatment effect by clinical doctors and medical technicians, and the text visiting records and the follow-up data by the doctors.

In clinical aspects i.e. in internal medicine department or surgery department, the medical treatment raw data comprise the patient identification information drafted and inputted by the doctors, such as the history of present illness, anamnesis, physical examination, laboratory detection, treating process after admission and so on. The medical treatment diagnosis data (also referred to target data) comprise the related records on initial diagnosis, discharge result and disease treatment effect by doctors.

Clinical Examples the medical treatment data analysis system is able to provide an analysis of disease identification, treatment advice and proposed treatment project after entering the corresponding admitted patient's relevant information, such as age, gender, weight, history of present illness, anamnesis, physical examination, laboratory detection, treating process after admission and then summarizing the analysis data. In a specific example, the related data on the patient is inputted as follows: 65 years old, male, cough, chest suppression, recent weight loss, long-term smoking history, and no previous detection.

In medical technology aspects (such as pathology, laboratory, radiology, nuclear medical and so on), the medical treatment raw data comprise original image data, pathological types, disease-related detection data, specific location of the lesion, and with or without transfer or dissemination. The medical treatment diagnosis data comprise the visiting records in text form and the follow-up data recorded by the doctors.

A specific example in medical technology in radiology department is that the intelligence analyser is able to identify and analyze the disease and provide further treatment advice by training the analysis of original image data on different body parts and using different image detection methods. In particular, the intelligence analyser is able to search all the original images in a very short period of time to determine the location, size, inner density, contour morphology, and the situation of other parts in the image of the lesion in a CT intelligence diagnosis of single pulmonary node disease.

The second step is to associate the variation value of the text data and image data which is not less than two-dimension of the medical treatment training data with the time and space with corresponding medical treatment diagnosis data. In other words, the second step is to associate the medical treatment raw data with the medical treatment diagnosis data of the same case.

The third step is to unify the medical treatment training data and the variation values of each subject into one unit data in the step of collecting the large amount of medical treatment training data, that is, to unify the medical treatment training data of one specific subject or related to a series of disease cases and the variation values into one unit data.

The fourth step is to transform or format the medical treatment training data into computer-understandable structured data matrix by segmentation, correlation or text data mining methods, and to extract features from each unit data, wherein the data features comprise the variation values of the medical treatment training data with time and space, and the varying mathematical statistics values of the data.

In particular, the data features comprise the variation of the medical treatment training data with the time-going, i.e., the decreasing or increasing trend of the data with respective to time-going and the variation of the medical treatment training data with the space-changing, i.e. the relationship of one image data from one pixel to the next. The data features further comprise the varying mathematical statistics values of the data, such as the comparison values between one individual data and other individual's. All the data features will be formatted as vectors, matrix, or array that is, transformed into a computer-understandable data structure.

The step of collecting the data features further comprises the steps of image processing or initial data processing. In the step of image processing for figuring out image data features, the first step is to segment out the image content related to the medical treatment diagnosis data.

In the step of textual document processing, the TF-IDF (term frequency-inverse document frequency) can be utilized as a quantized data retrieval and text mining method. The aforementioned text and image data processing methods would greatly facilitate the data features collection.

The fifth step is to input the medical treatment data formed as structured data matrix into a corresponding deep learning model of the computer device at a storage module thereof.

The sixth step is to optimize the deep learning model via the computer device, wherein the optimization method is described as following.

The first step of model optimization is to construct a primary deep learning frame and establish a data model comprising an input layer, at least a hidden layer and an output layer with respect to the data features of the medical treatment training data, wherein the input layer comprises a plurality of nodes with a plurality of data features of the medical treatment raw data, the output layer comprises a plurality of nodes with features of medical treatment diagnosis data, and each hidden layer comprises a plurality of nodes mapping with an output of the previous layer thereof.

The second step thereof is to establish a data model for each node using a mathematical formula, wherein the relevant parameters for the corresponding formulas are preset manually or at random automatically. The inputs to the nodes of the input layer are the data features of the medical treatment raw data, and the inputs to the nodes of the hidden layers and the output layer are the outputs generated at the previous layers respectively, wherein the outputs at each nodes of each layer is calculated according to the mathematical formula thereof.

The third step thereof is to initial the parameter Ai and comparing the output generated at each node of the output layer with the medical treatment diagnosis data stored at the respective node to modify the parameter Ai at the corresponding node thereby in a such a orderly-cycling manner to ultimately obtain a parameter Ai at the respective note which enables the output generated at the node of the output layer partial-maximally similar to the features of the medical treatment diagnosis data at corresponding node.

The methods to optimize the parameter Ai comprises supervised learning method and unsupervised learning method, wherein the unsupervised learning method uses a Denoising Autoencoder or Restricted Boltzmann Machine to self-learn.

More specifically, the mathematical formula can be a parametric mathematic formula or a non-parametric one, wherein the parametric formula can be linear model formula, neuron model formula or convolution formula, and the non-parametric one can be extreme formula. The mathematic model is constructed as follows:

$y = g(X) = fn \bigcirc fn-1 \bigcirc fn-2 \bigcirc \ldots \bigcirc f1(X)$, wherein the y is the features of the medical treatment diagnosis data at the output layer and the dimension thereof is $M_n$, the X is the medical treatment training raw data and the dimension thereof is $M_0$, and the $f_1$ to $f_n$ are the formulas for each layer, and the dimension for fi at the respective layer is $M_{i-1}$ to $M_i$, i.e., the f1 is arranged to transform the X in $M_0$-dimensioned into the $M_1$-dimensioned output $Z_1$, wherein the $Z_1$ becomes the input of the formula of $f_2$ and as such in a forward-propagation manner. The model $f_i$ at each layer has a parameter $A_i$ array matched therewith.

For example, the logical mathematic formula is given by:

$$y = \frac{\exp\left(\sum_{m \in M} x_m a_m\right)}{1 + \exp\left(\sum_{m \in M} x_m a_m\right)}.$$

Moreover, the linear model formula is given by:

$$y = \sum_{m \in M} x_m a_m,$$

wherein the $X_m$ is the input of the formula, the y represents the output thereof, and the am is the primary parameter thereof.

The parameters (From $A_1$ to $A_n$) and the depth of the deep learning model can be arbitrarily decided. Alternatively, the initialization parameters (From $A_1$ to $A_n$) for the deep learning model can be specific-set according to a particular method.

Detailed Description of the Operation Method.

The core of the model operation is supervised deep learning method, which is a revolutionary technology in the field of artificial intelligence and machine learning. Based on the DNN (Deep Neural Network) algorithm, the present invention ingeniously introduces the spatial and temporal variation of the lesion scan and takes the 3-D imaging regulations of the lesion into consideration to increase the probability of recognition. At the same time, the factor of doctors' human-judgment can also be introduced into the deep learning model, such that purely machine-judgment factor can be incorporated with the professional doctor-judgment factors to construct the model comprehensively and predict the lesion probability.

The present intention belongs to the artificial intelligence technology. The ultimate goal of the data operation is to "train" the model to assist doctors in the diagnosis and treatment by automatically recognizing the lesion from the medical treatment images, and indicating it with probability. Consequently, during the process of model construction, the large amount of data functions as teaching material and the architecture of the model play a role of abstracting these specific data according to the algorithms thereof. In other words, massive data and intelligence algorithms are two necessities in the intelligence data operation, which would be described in detail in the following.

1. Medical Treatment Training Data a) The medical treatment training data must be objective and non-make-up data generated in the actual diagnosis and treatment in the hospital. The closer the training data is to the medical treatment diagnosis data in actual application occasion, the better the training effect would be. The two kinds of data source, medical treatment raw data and medical treatment diagnosis data, are both essential for the realization of this patent. Moreover, the data which can be used as teaching material must meet the corresponding requirements. First, all the original medical treatment data, i.e. the image data by the medical treatment device in different formats, such as .nii.gz, .dcm, can be transformed into multi-dimensional matrix data prior to entering into the training model. For example, the MM (Magnetic Resonance Imaging) image can be transformed into 3-dimensional matrix comprising a two-dimensional grayscale index and one-dimensional cross section or four-dimensional matrix comprising a two-dimensional color index, three color index and one dimensional cross section. All the medical treatment data can be abstracted and simplified into such kind of matrix forming the raw model-readable data source.

Figure 2:
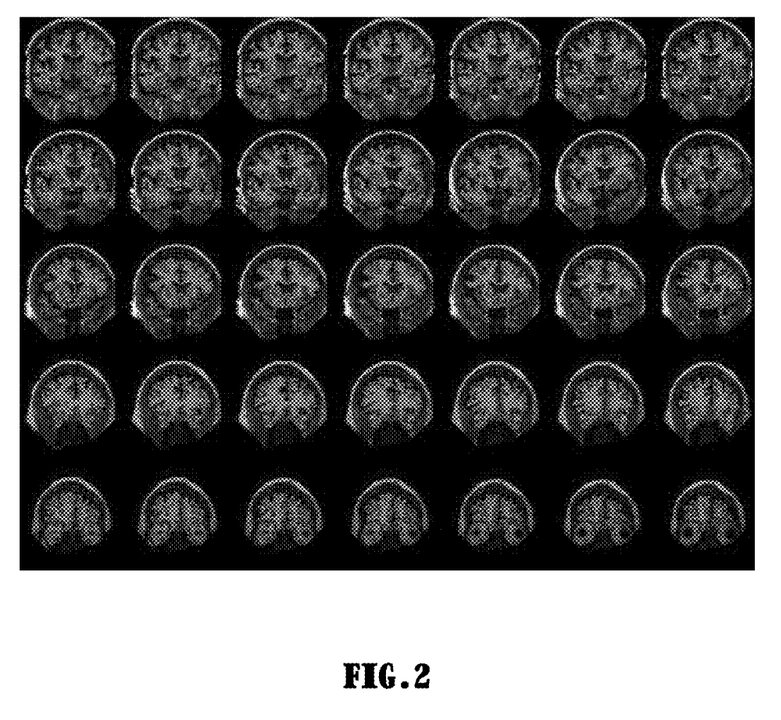
FIG. 2 illustrates an image data of brain MM.
Figure 3:
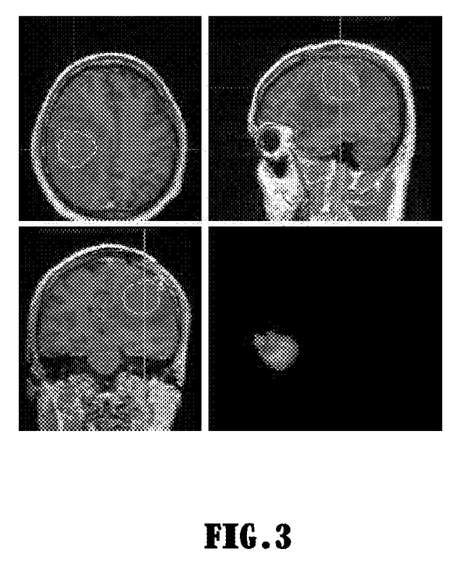
FIG. 3 illustrates a left image data after the objective data is deleted from the image data.

Referring to FIG. 2 and FIG. 3 of the drawings, a brain MM image data is illustrated. Suppose that the system can generate a 512×512 pixels picture from one MM slice and one brain-scan produces 200 MRI slices, that is, the data of one gray-scale brain-scan can be indicated as 512×512×200=52,428,800-dimension data rows covering all the abstracted and understandable information of the brain-scan.

In the unsupervised learning method, such medical treatment raw matrix is the fundamental data for model construction, while, in the supervised learning method, analysis goals matched with the images are further needed for modeling. The analysis goals can be as simple as binary analysis information, such as lesion measurement or the lesion probability detection (a little more complicated). Further, more complicated medical information such as the type of lesion, the treatment effect and the specific location of the lesion can be added as the analysis goals. It worth mentioning that for a even more complicated medical analysis system, such as a lesion development prediction system, the patient's historical physical examination results at a positive time sequence can be matched up for enabling the algorithm learn to predict the development of medical phenomena.

b) The medical treatment training data can be simulation data, which is formed by computer processing or simulation and functions as the training data for model construction.

One of the most-typical examples is the "Xbox Kinect system", wherein all the fundamental data are totally generated by 3-D modeling in the development phrase of hand-gesture recognition model construction.

In the present invention, the simulation data can be constructed by deforming, distorting, and noise-superimposing the original medical treatment data. There are two reasons for using the simulation data. Firstly, adding deformed data facilitates the algorithms to recognize the core varying regulation in the medical treatment data more stably. Secondly, since the DNN model needs to calculate millions of parameters generally, it is vulnerable to encounter over-fitting phenomenon in case that the data amount is limited. That is, the model over-learns historical data, and the core variation regulations cannot be well summarized and abstracted. Equivalent to adding noise in the training process, adding simulated deformation data to force the algorithm to better distinguish between noise and effective information is helpful to solve data over-fitting problems.

2. Machine Learning Algorithm Model

The machine learning algorithm model is a primary mathematical frame for information summarizing and abstraction, and the main purpose of which is to interpret the pattern recognition process into a computer-understandable mathematic structure. The "training" process of the model is to estimate the parameters thereof, and after the parameter estimation is completed, the model becomes the core part of method of the present invention. According to different purposes, the machine learning algorithm can be classified into supervised learning and unsupervised learning. The present invention covers both of the two types.

a) Supervised Learning

The supervised learning algorithms model attempts to search for a target regulation preset by human. As described above, besides the original image matrix data, analysis result data matched with the original data, such as medical diagnosis data, are further needed in the supervised learning algorithms.

The supervised learning algorithms included in this patent are described as follows.

i. Deep Neural Network

The fundamental theory of the DNN algorithm is to imitate the process of human-brain identification. By inputting original medical treatment data and the historical analysis of the doctors, the NDD algorithm is able to complete the analysis process automatically. As such, the DNN can be abstracted as $f(x)=y$, wherein x is the original medical treatment matrix data, y is the result of the intelligence analysing system and the formula f represents the mathematical mapping relationship between x and y [Note: this is only one kind of the above DNN models, wherein the first layer thereof is a convolution layer and the second layer thereof is a max-pooling layer in such a cycling manner.

The structure of DNN from the original image data side to the analysis result side can be divided into multiple layers, wherein each layer conducts different mathematic operations respectively. In other words, there are multiple neural layers in the model, wherein the first layer thereof completes a plurality of inner product calculation concurrently. The most common algorithm used in the first layer is convolution algorithm which slides a new formula at the original input data and outputs the inner product of the new formula and the original data. For example, in the 3D medical image recognition system, the DNN algorithm constructs a plurality of convolution blocks, each of which is a 3D matrix. The x and y axis of the convolution block covers a formula of spatial variation of the image and the z axis thereof covers a formula of the variation of the image in space. Each convolution block matrix is slid with respective to the data dimension so as to calculate the inner product between the values at respective dimension of the 3D image and the convolution blocks, wherein the values of the inner product can be loosely seen as the similarity between the data dimension and the convolution block, and the outputs generated at respective dimensions are the inputs of the successive neural layer respectively. From an intuitive perspective, the concurrent convolution matrix corresponds to a specific morphology, and the inner product calculation of the convolution matrix kind of determines whether different parts of the image data are similar to the specific morphology.

Figure 5:
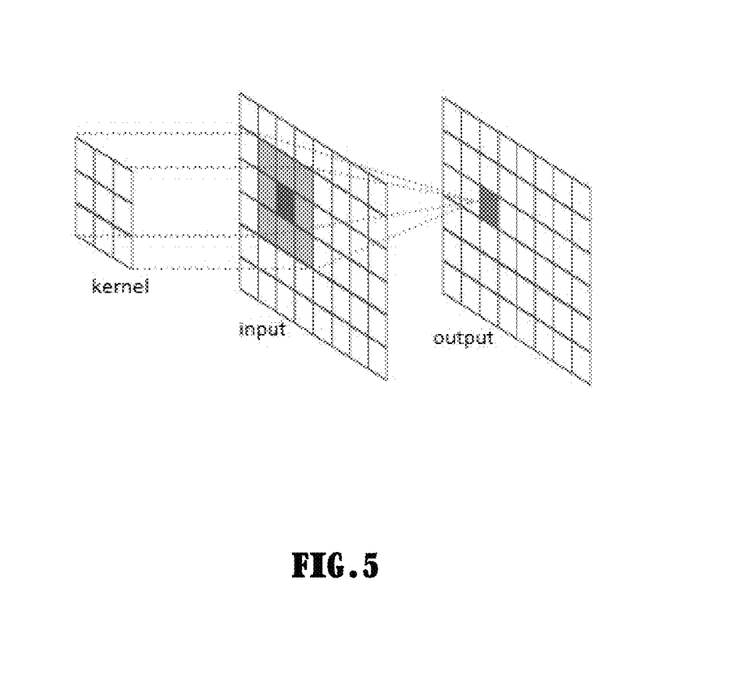
FIG. 5 is a schematic view of the operation of the convolution block.

As shown in FIG. 5, the second layer in the DNN model is commonly a layer to perform Max Pooling (MP)) operation. During the MP operation, the dimension information is synthesized into a wider-range block and the maximum calculation is performed in each block. The MP operation mainly learns from the features of active neurons in the visual neural network, that within a certain range of information frame, only the most active information unit is inputted into the successive layer. From a graphical perspective, the MP operation remains the calculation results unchanged regardless of the data rotation. From an operational view, the MP operation is to reduce the dimensionality of an input representation. In particular, combining with the first neural layer operation, the region with a low similarity to the convolution block in the first convolution layer is removed so as to reduce the proportion of the invalid information in each region.

Figure 4:
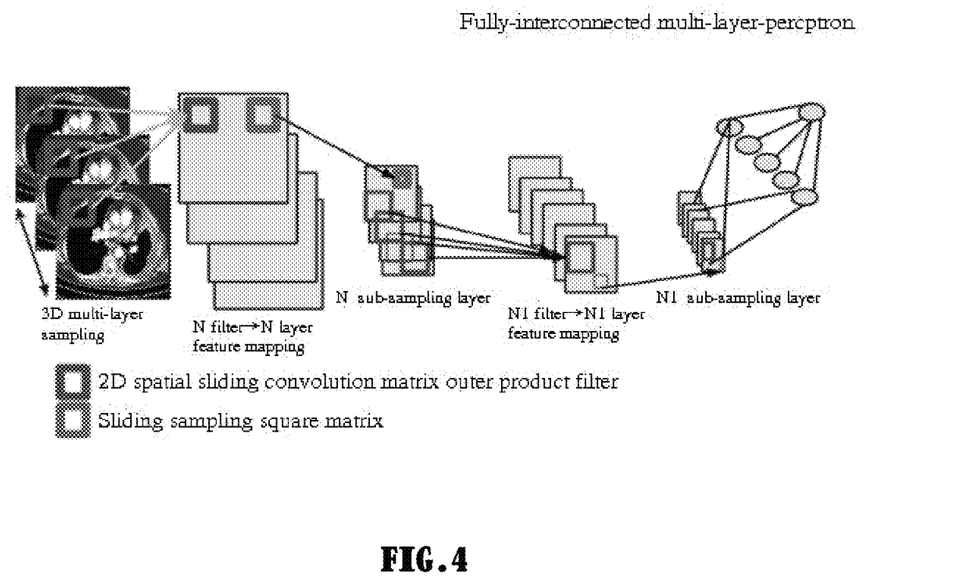
FIG. 4 is a schematic view of the basic mathematical structure of the DNN based on image data.

The structure of DNN is generally the combination and the repetition of the convolution layer and the max polling layer, which is aimed to extract features related to the medical treatment-or-diagnosis-related data. Intuitively speaking, as shown in the FIG. 4, the algorithm of a medium layer uses a nonlinear combination of the first layer and second layer feature, and as such to construct a more abstracted frame. According to the method disclosed in the patent, countless neural layers can be constructed.

Theoretically speaking, the larger amount of the repetition of the combination is, the better effect the model training will be, in case that massive data can be got for training. Although, the operation system of the human brain has not yet been fully perceived, it is already known that the human brain has a very deep neural network structure. Consequently, the deeper the neural model is, more effective the model would be. However, deeper-layer neural model needs more parameters which are more difficult to train and estimate, and the issues of vanishing gradient and overfitting would arise easily.

Figure 6:
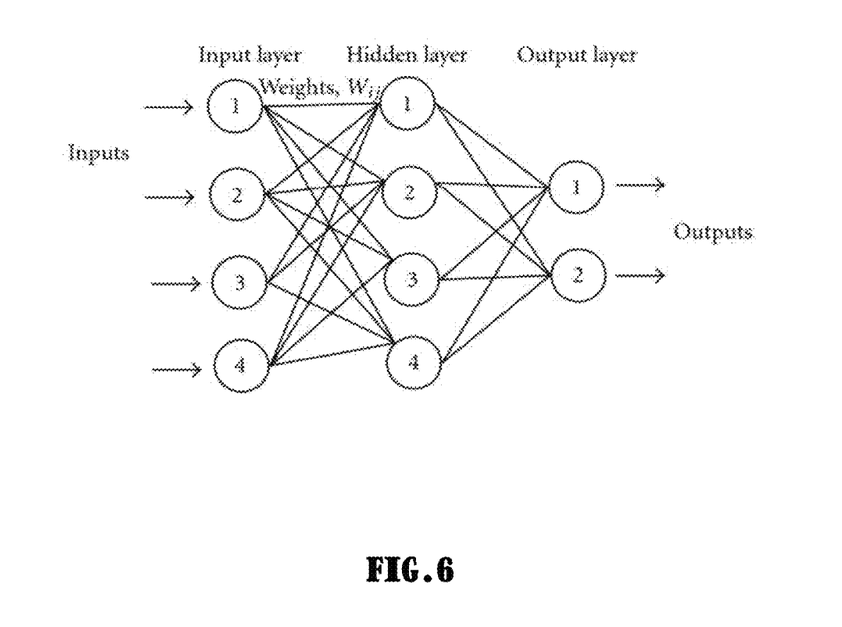
FIG. 6 is a schematic view of the operation of the full-interconnected multi-layer-perceptron.

After undergoing many convolution and Max pooling operations, the left information is entered into a full-interconnected multi-layer-perceptron. The basic structure of the MLP comprises two layers of logical regression operations attempting to assign different abstract graphic elements contributing to the final judging result, and the ultimate output of the MLP operation is the medical treatment analysis result of the model. As shown in FIG. 6, the MLP is commonly a hidden-perceptron layer, wherein the variables at a successive layer are fully-interconnected with those at the previous layer thereof, and the output logically calculated at the previous layer are the inputs of the successive layer for calculating the outputs thereat correspondingly.

b) Unsupervised Learning

The concept of neural networks has been prevalent for many years. However, restricted by the amount of accessible data and the operation ability of the processor, the vanishing gradient issue is very serious, and thus the DNN is unable to solve practical problem. Moreover, during a completed model training process, the difference between the predication outputs generated by the model and the true value forms the basis of model parameter optimization. However, an overly-deep neural network structure is unable to backpropagate the parameter optimization information to the bottom network layer. In other words, the information at the top layer is unable to be downward transferred into the deep network structure layer by layer, which brings great difficulties for model construction, especially, in the field of medical treatment data analysis. The amount of medical treatment data is generally very large and the difficult in the operation is more severe than other field. Therefore, it is unrealistic to conduct a complete parameter optimization search in the medical treatment data analysis field. In the present invention, the parameters in the model are initially optimized through the unsupervised learning method to provide a better initial condition for the parameter optimization, such that the local minimum parameter of the model can be figured out more quickly in the parameter optimization process.

It is well known that the two best unsupervised learning methods are denoising Autoencoders (dAE) and Restricted Boltzmann Machine (BRM).

i. Denoising Autoencoders (DAE)

Figure 7:
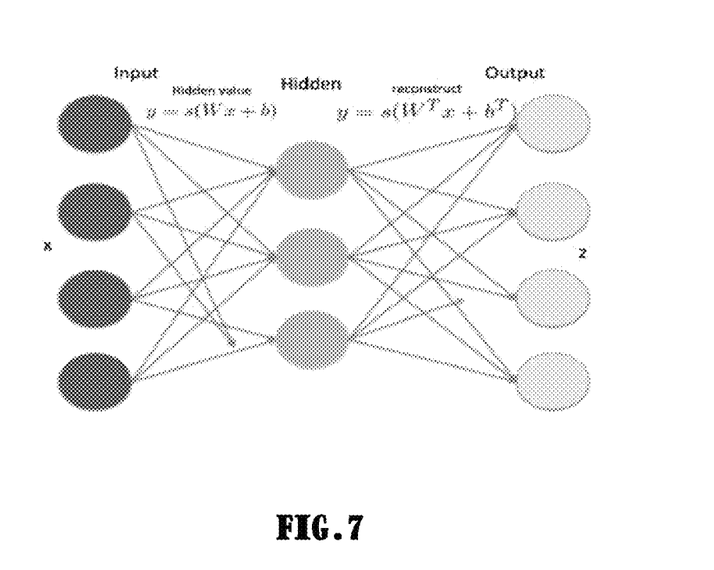
FIG. 7 is a schematic flowchart of the operation of the Autoencoder.

The principle of the autoencoder is to find out an effective latent variable for a data set. Referring to the FIG. 7 of the drawings, the completed operation process of the autoencoder is illustrated, wherein the autoencoder searches for a latent variable W mapping with a new data Z, according to the original medical treatment data, and the ultimate purpose of the autoencoder is to figure out the parameter W which minimizes the difference between z and x. In other words, the goal of the autoencoder is to find out a parameter to fully represent the whole data variables within the limited information. The DAE introduce a large amount of noise manually into the operation of the autoencoder. Intuitively speaking, the large amount of noise is used to force the model to search for more valuable potential regulations without being affected by invalid regulations in the noise. The ultimately-trained parameters would be the initial parameters for supervised learning so as to provide a better starting point for the model construction to speed up the parameter optimization thereby.

ii. Restricted Boltzmann Machine (BRM)

The BRM plays a similar role as the DAE in preparing for the parameter optimization in unsupervised learning. Much like the DAE, the RBM attempts to find out a best representation for the original data variables as the initial parameters for the supervised learning later on. However, unlike with the DAE, the RBM uses energy-probabilistic generative models instead of definite mathematical formula of DAE. From the computational perspective, the RBM is more complicated than DAE. But the nature of the probabilistic generative models is more fitted in the model application which is intended on event probability prediction. In order to reduce the generation of over-fitting as far as possible, the two types of unsupervised learning methods, the RBM and DAE, are both utilized in our deep learning and model construction.

A further step to optimize the parameter is to establish a loss function or objective function, by which to conduct the parameter optimization in the supervised learning data model. The loss function can be a function of the difference between the analysis result generated by the deep learning model and the true objective values. During the operation of the loss function, the parameters in the model are adjusted according to the changes of the loss function and the optimization method. In a specific application of the medical imaging cardiovascular cross-section area measurement, the loss function can be set as a function of the difference (such as variance difference) between the detection values generated by the model and the true values, and the parameters are shifted in each loop of the optimization process according to a gradient descent parameter optimization method. The process of parameter optimization is stopped until the parameter optimization meets certain conditions, i.e. the value of the loss function less than a preset threshold or the amount of the cycling exceeding a certain value, and then keep the relative best parameter.

The optimization process of the objective function can be described as:

$$O^* = \min_A O(A, X) = \min_A \{L[Y, g(X, A)] + \lambda R(A)\},$$

wherein the g(x, A) is the analysis output generated by the deep learning model, Y is the true values of the analysis objective and the L[Y, g(X,A)] is mainly for calculating the cost of the difference between the analysis output generated by the deep learning model and the true values of the analysis objective.

Relatively common L[Y, g(X, A)] is given by:

$$\Sigma_i |y_i - g_i(x_i, A)| \text{ or } L[Y, g(X, A)] = \Sigma_i [y_i - g_i(x_i, A)]^2.$$

The R(A) is a regular expression mainly for avoiding over-fitting of the model. Relatively common regular expression is given by L1: $R(A) = \Sigma_{a \in A} |a|$ or L2: $R(A) = \Sigma_{a \in A} a^2$. It worth mentioning that the user can pick another other regular expression.

The parameter optimization method can be arbitrarily selected and the most commonly-used one is gradient descent method, which can be defined as:

$A_{j+1} = A_j - \gamma \nabla O(A_j, X)$, wherein the parameter of the objective function is moved against the differential direction for j rounds and would be stopped until meeting certain conditions.

A further step to optimize the data is add some noise into the data or model intentionally to stabilize the mode and reduce the over-fitting problems of the data model. For example, in the medical image intelligence analyser, noise can be added into the analyzer by deforming or distorting the original data to force the model to recognize the effective information without being affected by the invalid noise.

A further step to optimize the data is the test sample segmentation. In particular, part of the training data can be further segmented into test sample, and the left data is utilized to construct the deep learning model in such a manner that the test sample can be utilized to test the validity of the model so as to adjust the core frame of the deep learning model automatically or manually based on the testing results.

The seventh step is to input the obtained to-be-analyzed medical data formed as structured matrix data, into the deep learning model to conduct a medical pathological analysis matched therewith.

The eighth step is to output a medical pathological analysis result matched with the to-be-analyzed medical data by the deep learning model via an output device.

The ninth step is to feed the structured data of the to-be-analyzed medical data and the analysis result matched with the to-be-analyzed data back to the deep learning model as new training data.

The present invention provides an intelligent analyzer for analyzing medical treatment data based on deep learning, comprising:

an inputting means for inputting the medical treatment training data and the to-be-analyzed medical data into a computer device;

an storage module for storing the medical treatment training data and the to-be-analyzed data separately or collectively;

a deep learning model module for calling the medical treatment training data stored at storage model for self-learning;

an outputting means for outputting the medical pathological analysis result matched with the to-be-analyzed medical data; and a CPU and/or GPU processor, wherein the medical treatment training data comprise a medical raw data and a medical treatment diagnosis data matched therewith and the medical treatment training data and the to-be-analyzed medical data are computer-understandable structured data matrix, wherein the self-learning of deep learning model module uses the parametrical mathematical formulas including linear model formula, neuron model formula, convolution formula, and/or extreme formulas, wherein the inputting means comprises computer devices provided at hospitals or medical research institutions, and various of medical detection device and pathological analysis device networked with the computer devices, such as computers, ultrasound equipment, X-ray equipment, dynamic electrocardiogram instrument, biochemical analyzer, immunity analyzer, fiber endoscopy, MM, CT Doppler diagnostic apparatus, sphygmomanometer and scales, wherein the output means comprises stationary computing output terminals and portable intelligent terminals provided at hospitals and medical research institutions and networked with the inputting means, such as computers, medical equipment terminals and mobile terminals.

In order to share resources in the hospital or medical institution, a network linking module for linking to the internet or Ethernet by means of wire, WIFI model or GPRS module is mounted at the intelligent analyzer of the present invention.

The deep learning model, which is trained by the intelligence analyser, is put into actual applications as a completed integrated system. The new medical treatment data (the to-be-analyzed medical data) generated is combined with the parameters of the model to get a medical analysis prediction result. In the actual applications, the intelligence analyser can be used as extra add-ons in the analysis process. According to the different applications, the intelligence analyser can be used as a extra plug-in for medical treatment devices, or used as a plug-in interface for the common PACS (picture archiving and communication system) or HIS (hospital information system). Alternatively, the analysis reports generated by the intelligence analyser can be import into other system through internet interface.

One skilled in the art will understand that the embodiment of the present invention as shown in the drawings and described above is exemplary only and not intended to be limiting.

It will thus be seen that the objects of the present invention have been fully and effectively accomplished. The embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. A method for analyzing medical treatment data based on deep learning, comprising the following steps:

1) collecting and storing registered medical treatment raw data and medical diagnosis raw data which are matched and of the same type with the medical treatment raw data as medical treatment training data at a computer device via an input device, wherein the medical treatment raw data comprise related records on patient diagnosis, detection and treatment by clinical doctors and medical technicians;

2) linking a variation value of textual data and image data which is not less than two-dimension in the medical treatment training data with time and space with the corresponding data;

3) unifying the medical treatment training data and the variation value of each subject into one unit data in the step of collecting the large amount of medical training data;

4) transforming or formatting the medical treatment training data into computer-understandable structured data matrix by segmentation, correlation or text data mining methods, and extracting features from each unit data;

5) inputting the medical treatment data formed as structured data matrix into a corresponding deep learning model of the computer device at a storage module thereof;

6) optimizing the deep learning model via the computer device, comprising the following steps:
a. constructing a primary deep learning frame to establish a data model comprising an input layer, at least a hidden layer and an output layer, according to the features of the medical treatment training data, wherein the input layer comprises a plurality of nodes having a plurality of features of the medical treatment raw data, the output layer comprises a plurality of nodes with a plurality of features of the medical treatment diagnosis data, and each hidden layer comprises a plurality of nodes mapping with an output from a previous layer thereof, wherein the medical treatment diagnosis data comprise related records on initial diagnosis, discharge result and disease treatment effect by clinical doctors and medical technicians, and textual visiting records and the follow-up data by doctors;
b. constructing the data model for each of the nodes with a mathematical formula, wherein related parameters for the mathematical formula are preset manually or at random automatically, inputs to the nodes of the input layer are the features of the medical treatment raw data, and inputs to respective hidden layer and the output layer are outputs generated at the previous layer thereof respectively, wherein the outputs at each node of each layer is obtained according to the mathematical formula thereof; and
c. via an unsupervised learning method, initializing a parameter Ai and comparing the output generated at each node of the output layer with the medical treatment diagnosis data stored at the respective node, and via a supervised learning method, modifying the parameter Ai at the node thereby in an orderly-cycling manner to ultimately obtain the parameter Ai at the respective node which enables the output generated at the respective node of the output layer at its partially maximum of the corresponding node similar to the features of the medical treatment diagnosis data;

7) inputting obtained to-be-analyzed medical data formed as structured matrix data, into the deep learning model to conduct a medical pathological analysis matched therewith; and 8) outputting a medical pathological analysis result matched with the to-be-analyzed medical data by the deep learning model through an output device;

wherein data features of the medical treatment training data comprise a spatial and temporal variation of a lesion during a process from initial diagnosis to disease treatment and then to hospital discharge;

wherein the medical pathological analysis result comprises an analysis of disease identification, treatment advice and proposed treatment project;

wherein the deep learning model is trained to perform an intelligence diagnosis of pulmonary diseases.

2. The method as recited in claim 1, wherein the unsupervised learning method is selected from the group consisting of Denoising Auto encoder and Restricted Boltzmann Machine.

3. The method as recited in claim 1, wherein the mathematical formula is one of a parametric formula and a non-parametric formula, wherein the parametric formula is one of a linear model formula, a neuron model formula and a convolution operation, and the non-parametric formula is an extreme formula, wherein a mathematic model is constructed as follows:

$y=g(X)=fn \bigcirc fn-1 \bigcirc fn-2 \bigcirc \ldots \bigcirc f1(X)$, wherein y is the features of the medical treatment diagnosis data at the output layer and a dimension thereof is $M_n$, X is training raw data and a dimension thereof is $M_0$, and f1 to fn are the formulas for each layer, and the dimension for fi at the respective layer is Mi−1 to Mi, i.e., the f1 is arranged to transform X in M0-dimensioned into M1-dimensioned output Z1, wherein Z1 is the input of the formula at f2 and as such in a forward-propagation manner, wherein the model fi at each layer has a parameter Ai array matched therewith.

4. The method as recited in claim 1, wherein structured data of the to-be-analyzed medical data and medical analysis data matched therewith are fed back to the deep learning model as new training data.

5. The method as recited in claim 1, wherein a simulation data is constructed by deforming, distorting, and noise-superimposing the medical treatment training data before inputting the medical treatment training data into the corresponding deep learning model of the computer device at a storage module.

6. The method as recited in claim 1, wherein the medical pathological analysis result further comprises a type of lesion, the treatment effect and the specific location of the lesion.

7. The method as recited in claim 1, wherein the deep learning model is trained to learn to predict the development of medical phenomena.

8. An intelligent analyzer for analyzing medical treatment data based on deep learning, comprising:
an inputting means for inputting medical treatment training data and to-be-analyzed medical data into a computer device;
a storage module for storing the medical treatment training data and the to-be-analyzed data separately or collectively;
a deep learning model module for calling the medical treatment training data stored at storage model for self-learning;
an outputting means for outputting a medical pathological analysis result matched with the to-be-analyzed medical data; and
a central processing unit (CPU) and/or graphics processing unit (GPU) processor, wherein the medical treatment training data comprise a medical treatment raw data and a medical treatment diagnosis data matched therewith and the medical treatment training data and the to-be-analyzed medical data are computer-understandable structured data matrix, wherein the self-learning of deep learning model module uses parametrical mathematical formulas including at least one of linear model equation, neuron model equation, convolution equation, and extreme formulas, wherein the inputting means comprises computer devices for being provided at hospitals or medical research institutions, and stationary computing output terminals and portable intelligent terminals networked with the computer devices, wherein the output means comprises stationary computing output terminals and portable intelligent terminals for being provided at hospitals and medical research institutions and networked with the inputting means, wherein the medical treatment raw data comprise related records on patient diagnosis, detection and treatment by clinical doctors and medical technicians, wherein the medical treatment diagnosis data comprise related records on initial diagnosis, discharge result and disease treatment effect by clinical doctors and medical technicians, and textual visiting records and the follow-up data by doctors;

wherein the deep learning model is optimized and configured by at least one of the CPU and GPU processor to:

construct a primary deep learning frame to establish a data model comprising an input layer, at least a hidden layer and an output layer, according to the features of the medical treatment training data, wherein the input layer comprises a plurality of nodes having a plurality of features of the medical treatment raw data, the output layer comprises a plurality of nodes with a plurality of features of the medical treatment diagnosis data, and each hidden layer comprises a plurality of nodes mapping with an output from a previous layer thereof, construct the data model for each of the nodes with a mathematical formula, wherein related parameters for the mathematical formula are preset manually or at random automatically, inputs to the nodes of the input layer are the features of the medical treatment raw data, and inputs to respective hidden layer and the output layer are outputs generated at the previous layer thereof respectively, wherein the outputs at each node of each layer is obtained according to the mathematical formula thereof; and via an unsupervised learning method, initialize a parameter Ai and compare the output generated at each node of the output layer with the medical treatment diagnosis data stored at the respective node, and via a supervised learning method, modify the parameter Ai at the node thereby in an orderly-cycling manner to ultimately obtain the parameter Ai at the respective node which enables the output generated at the respective node of the output layer at its partially maximum of the corresponding node similar to the features of the medical treatment diagnosis data;

wherein data features of the medical treatment training data comprise a spatial and temporal variation of a lesion during a process from initial diagnosis to disease treatment and then to hospital discharge;

wherein the medical pathological analysis result comprises an analysis of disease identification, treatment advice and proposed treatment project;

wherein the deep learning model is trained to perform an intelligence diagnosis of pulmonary diseases.

9. The intelligent analyzer as recited in claim 8, further comprising:

a network linking module for linking to the internet or Ethernet by means of wire, wireless fidelity (WIFI) model and general packet radio service (GPRS) module.

10. The intelligent analyzer as recited in claim 8, wherein each the parametrical mathematical formula is one of a parametric formula and a non-parametric formula, wherein the parametric formula is one of a linear model formula, a neuron model formula and a convolution operation, and the non-parametric formula is an extreme formula, wherein a mathematic model is constructed as follows:

$y=g(X)=fn \bigcirc fn-1 \bigcirc fn-2 \bigcirc \ldots \bigcirc f1(X)$, wherein y is the features of the medical treatment diagnosis data at the output layer and a dimension thereof is $M_n$, X is training raw data and a dimension thereof is $M_0$, and f1 to fn are the formulas for each layer, and the dimension for fi at the respective layer is Mi−1 to Mi, i.e., the f1 is arranged to transform X in M0-dimensioned into M1-dimensioned output Z1, wherein Z1 is the input of the formula at f2 and as such in a forward-propagation manner, wherein the fi at each layer has a parameter Ai array matched therewith.

11. The intelligent analyzer as recited in claim 9, wherein each the parametrical mathematical formula is one of a parametric formula and a non-parametric formula, wherein the parametric formula is one of a linear model formula, a neuron model formula and a convolution operation, and the non-parametric formula is an extreme formula, wherein a mathematic model is constructed as follows:

$y=g(X)=fn \bigcirc fn-1 \bigcirc fn-2 \bigcirc \ldots \bigcirc f1(X)$, wherein y is the features of the medical treatment diagnosis data at the output layer and a dimension thereof is $M_n$, X is training raw data and a dimension thereof is $M_0$, and f1 to fn are the formulas for each layer, and the dimension for fi at the respective layer is Mi−1 to Mi, i.e., the f1 is arranged to transform X in M0-dimensioned into M1-dimensioned output Z1, wherein Z1 is the input of the formula at f2 and as such in a forward-propagation manner, wherein the fi at each layer has a parameter Ai array matched therewith.

12. The intelligent analyzer as recited in claim 8, wherein a simulation data is constructed by deforming, distorting, and noise-superimposing the medical treatment training data before inputting the medical treatment training data into the deep learning model module for calling the medical treatment training data stored at storage model for self-learning.

13. The intelligent analyzer as recited in claim 8, wherein the medical pathological analysis result further comprises a type of lesion, the treatment effect and the specific location of the lesion.

14. The intelligent analyzer as recited in claim 8, wherein the deep learning model is trained to learn to predict the development of medical phenomena.

* * * * *